United States Patent
Takenaka et al.

(10) Patent No.: US 9,211,055 B2
(45) Date of Patent: Dec. 15, 2015

(54) CAPSULE TYPE MEDICAL DEVICE

(75) Inventors: Tomoya Takenaka, Oita (JP);
Masatoshi Homan, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 1573 days.

(21) Appl. No.: 12/437,210

(22) Filed: May 7, 2009

(65) Prior Publication Data

US 2009/0281401 A1    Nov. 12, 2009

(30) Foreign Application Priority Data

May 7, 2008    (JP) ................................. 2008-121514

(51) Int. Cl.
| | | |
|---|---|---|
| *A61B 1/00* | (2006.01) | |
| *A61B 1/04* | (2006.01) | |
| *A61B 5/07* | (2006.01) | |

(52) U.S. Cl.
CPC ............. *A61B 1/041* (2013.01); *A61B 1/0011* (2013.01); *A61B 1/00016* (2013.01); *A61B 5/07* (2013.01)

(58) Field of Classification Search
None
See application file for complete search history.

(56) References Cited

U.S. PATENT DOCUMENTS

| | | | | |
|---|---|---|---|---|
| 2006/0224040 | A1* | 10/2006 | Khait et al. | 600/102 |
| 2006/0241422 | A1* | 10/2006 | Muratayev et al. | 600/435 |
| 2007/0100208 | A1 | 5/2007 | Lewkowicz | |
| 2007/0156015 | A1* | 7/2007 | Gilad | 600/102 |

FOREIGN PATENT DOCUMENTS

| | | |
|---|---|---|
| EP | 1 707 102 A1 | 10/2006 |
| EP | 1 707 105 A1 | 10/2006 |
| JP | 2005-205072 A | 8/2005 |
| JP | 2005-329247 | 12/2005 |
| JP | 2006-280940 A | 10/2006 |
| JP | 2006-280954 A | 10/2006 |
| JP | 2006-297080 A | 11/2006 |
| JP | 2007-195961 A | 8/2007 |
| JP | 2007-229490 A | 9/2007 |
| JP | 2008-67131 A | 3/2008 |
| WO | WO 2008/035760 A1 | 3/2008 |

OTHER PUBLICATIONS

Notice of Rejection dated Jan. 15, 2013 from corresponding Japanese Patent Application No. 2008-121514 together with an English-language translation.

* cited by examiner

*Primary Examiner* — Isaac Shomer
(74) *Attorney, Agent, or Firm* — Scully, Scott, Murphy & Presser, PC

(57) ABSTRACT

A capsule type medical device having a substrate section that includes at least a single layer substrate; an antenna conductor that is arranged on and closely attached to at least one surface of the substrate section; a transmitting circuit that is arranged on the one surface of the substrate section within an area surrounded by the antenna conductor; and a plurality of lands that are arranged to another surface of the substrate section, and electrically connected with the transmitting circuit.

11 Claims, 9 Drawing Sheets

CAPSULE TYPE MEDICAL DEVICE

CROSS-REFERENCE TO RELATED APPLICATIONS

This application is based upon and claims the benefit of priority from Japanese Patent Application No. 2008-121514, filed May 7, 2008, the entire contents of which are incorporated herein by reference.

BACKGROUND OF THE INVENTION

1. Field of the Invention

The present invention relates to a capsule type medical device having an antenna.

2. Description of the Related Art

In recent years, the capsule type medical device that is inserted into the body of a subject and conducts an intra-subject observation, examination, and medical cure or medical treatment has been in practical use. The capsule type medical device includes a capsule type casing, and internal components, such as an imaging unit, a transmitting unit, an antenna, or an electric power source, which are housed in the capsule type casing. As such a capsule type medical device, a capsule endoscope is known, and as the capsule endoscope, there is a swallowable capsule which is described, for example, in Japanese Patent Application Laid-Open No. 2005-329247.

SUMMARY OF THE INVENTION

A capsule type medical device according to one aspect of the present invention includes a substrate section that includes at least a single layer substrate, an antenna conductor that is arranged on and closely attached to at least one surface of the substrate section, a transmitting circuit that is arranged on the one surface of the substrate section within an area surrounded by the antenna conductor, and a plurality of lands that are arranged to another surface of the substrate section, and electrically connected with the transmitting circuit.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
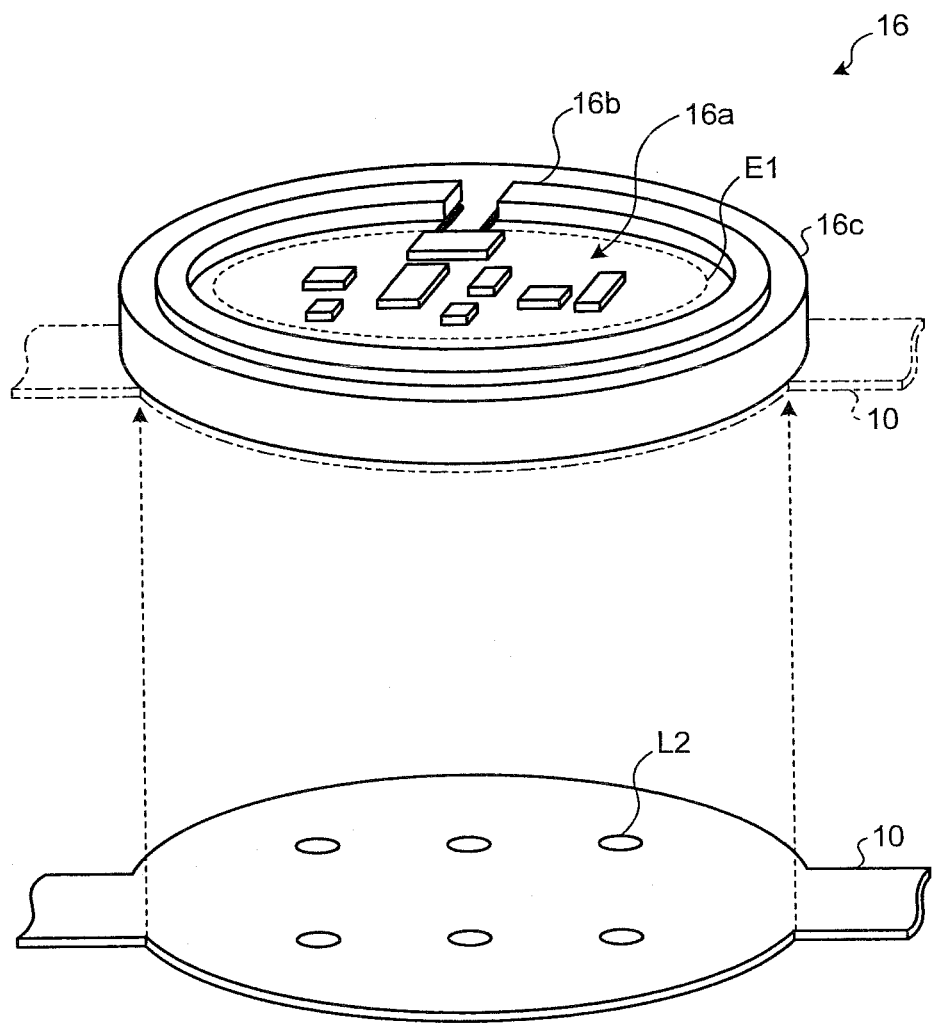
FIG. 1 is a perspective view of a radio communication unit that is viewed from above at an oblique angle.

A capsule type medical device includes an antenna which is used to transmit information acquired by the components of the capsule type medical device to outside, and to receive information given from the outside and transfer the received information to the components. The inventors of the present invention focused their attention on the fact that the conventional antenna housed in the capsule type medical device is cubic in shape, and therefore there exists dead space inside the antenna as illustrated in FIG. 1 of Japanese Patent Application Laid-open No. 2005-329247. The inventors of the present invention found that it is possible to provide more space by reducing or eliminating the dead space.

Figure 2:
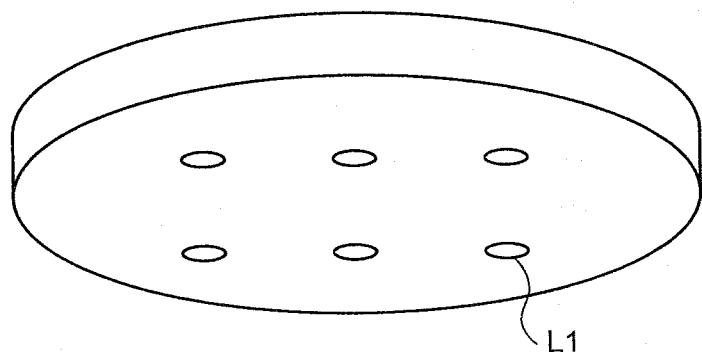
FIG. 2 is a perspective view of the radio communication unit that is viewed from below at an oblique angle.

The present invention is explained referring to FIG. 1 and FIG. 2. However, the present invention is not limited to FIG. 1 and FIG. 2. The present invention is a capsule type medical device that includes a substrate section 16c that has at least a single layer substrate, an antenna conductor 16b, a transmitting circuit 16a, and lands arranged on one surface of the substrate section 16c and electrically connected to the transmitting circuit 16a. The antenna conductor 16b is arranged so as to be closely attached to at least one surface of the substrate section 16c. The transmitting circuit 16a is arranged on one surface of the substrate section 16c within an area E1 surrounded by the antenna conductor 16b.

A unit that includes the substrate section 16c, the antenna conductor 16b, the transmitting circuit 16a, and the lands is hereinbelow referred to as a radio communication unit 16. The radio communication unit 16 is capable of, for example, transmitting information obtained by components such as an imaging unit of the capsule type medical device to the outside, or receiving information given from the outside and transferring the received information to the components of the capsule type medical device. FIG. 1 is a perspective view of the radio communication unit 16 that is viewed from above at an oblique angle, and FIG. 2 is a perspective view of the radio communication unit 16 that is viewed from below at an oblique angle.

As illustrated in FIG. 1, the antenna conductor 16b is arranged so as to be closely attached to at least one of the surfaces of the substrate section 16c that holds the transmitting circuit 16a, whereby the dead space, which exists inside the conventional antenna, can be reduced or eliminated. The dead space can be further reduced by arranging the transmitting circuit 16a within the area E1 surrounded by the antenna conductor 16b. Moreover, because the antenna conductor 16b is closely attached to the substrate section 16c, the antenna hardly deforms, whereby handling ability of the antenna improves. Thus, an automatic mounting of the substrate, on which the antenna is arranged, is possible with the reflow soldering and the like. Therefore the productivity of the antenna and the capsule type medical device improves, and the manufacturing cost of the antenna and the capsule type medical device can be reduced. Furthermore, by conducting performance tests of the antenna before connecting the radio communication unit 16 to other components and after the final assembly, performance tests of the antenna are not required after each assembly process performed after the mounting of the radio communication unit 16, thus the testability improves and the test cost can be reduced.

Each of the components of the radio communication unit is described in detail below.

——Substrate Section——

In the present invention, the substrate section at least plays roles of holding the antenna conductor and holding the transmitting circuit.

Material of the substrate section is not particularly limited. For example, glass epoxy, paper phenol, paper epoxy, glass composite, Teflon®, alumina, composite, photo-solder resist, liquid crystal polymer, or polyimide may be used.

A single layer substrate suffices as the substrate section. The substrate section may, however, include plural substrates stacked one on another, depending on the purposes. For example, if it is required to form the antenna conductor cubically by closely attaching the antenna conductor to the substrate section, it is possible to employ a substrate section including a plurality of substrates. The cubic antenna conductor is explained later in detail in "Antenna Conductor" section. Moreover, it is also possible to increase the density of the wiring by increasing the number of substrate layers that form the substrate section.

Figure 6A:
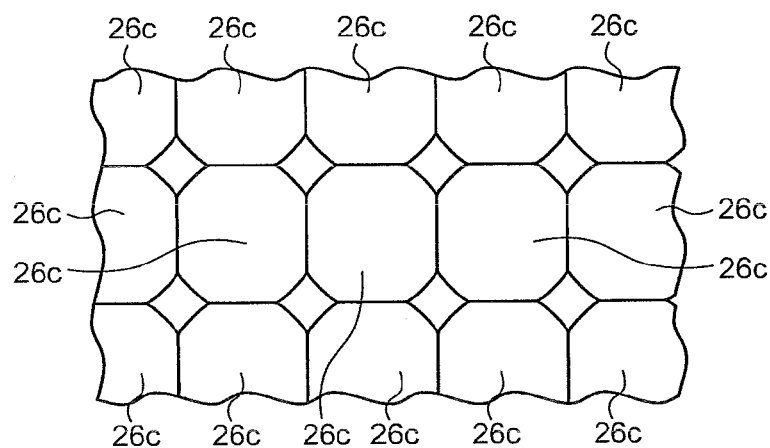
FIGS. 6A to 6D are schematic diagrams of an example of a shape of the substrate section.
Figure 6B:
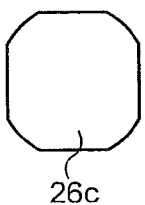
Figure 6C:
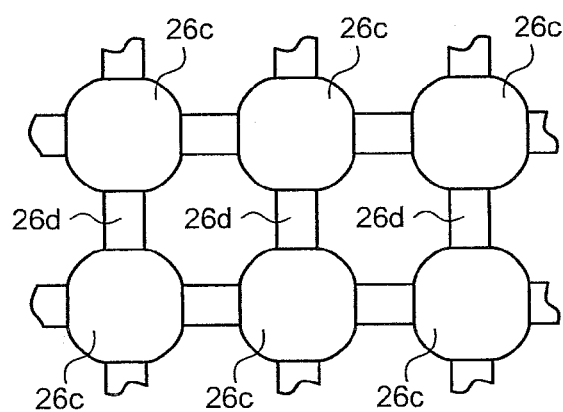
Figure 6D:
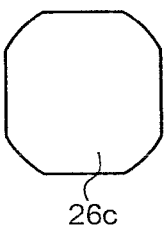

The shape of the substrate section is not particularly limited, and can be appropriately decided depending on the shape of casing of the capsule type medical device, and shapes and layout of the components that form the capsule type medical device. Preferably, however, the substrate section is circular disk shape. In the present invention, the "circular disk shape" is not limited to the shape that is illustrated in FIG. 1, and includes the shape of a substrate section 26c illustrated in FIGS. 6B and 6D. The substrate section 26c can be obtained by forming a plate as illustrated in FIGS. 6A and 6C and subsequently cutting joint portions (i.e., portions denoted by sign 26d in FIG. 6C). This manner of substrate formation is preferable, because it can improve the productivity of the substrate section.

Thickness of the substrate section is not particularly limited, but can be appropriately decided based on the purpose.

Size of the substrate section is not particularly limited, but can be appropriately decided based on the purposes.

——Antenna Conductor——

The material of the antenna conductor used in the present invention is not particularly limited, but conventionally known conductive materials may be used. For example, copper, silver, gold, alloys, or conductive adhesive may be used. Among alloys, brass and solder are particularly preferable. Among conductive adhesive, a combination of epoxy resin and silver is preferable.

Shape of the antenna conductor is not limited, and can be appropriately decided depending on the purposes. However, a C-shaped antenna conductor denoted by 16b in FIG. 4 and a spiral-shaped antenna conductor denoted by 26b in FIG. 5 are preferable. The spiral-shaped antenna conductor has, preferably 1.5 to 2.5 turns, and more preferably 2 turns. However, the shape of the antenna conductor of the present invention is not limited to those illustrated in FIG. 4 and FIG. 5. The shape of the antenna conductor can be appropriately decided depending on purposes such as degrees of curve of the antenna conductor. It is preferable to make the antenna conductor C-shaped or spiral-shaped because such antenna conductor is almost circular in shape and able to realize an antenna with less directionality like a loop antenna. The C-shaped antenna and the spiral-shaped antenna also have a function as an inductor. Therefore, the antenna may be used not only as an antenna, but also as an inductor of a tuned circuit.

The shape of the antenna conductor may be planar, or cubic. A cubic antenna conductor may be so formed that the antenna conductor is partly embedded in the substrate section.

Figure 4:
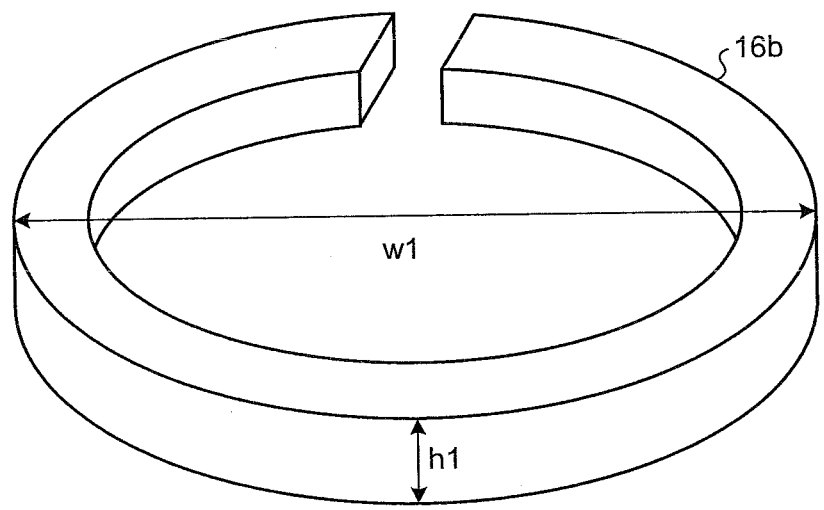
FIG. 4 is a perspective view that illustrates a structure of an antenna conductor.
Figure 5:
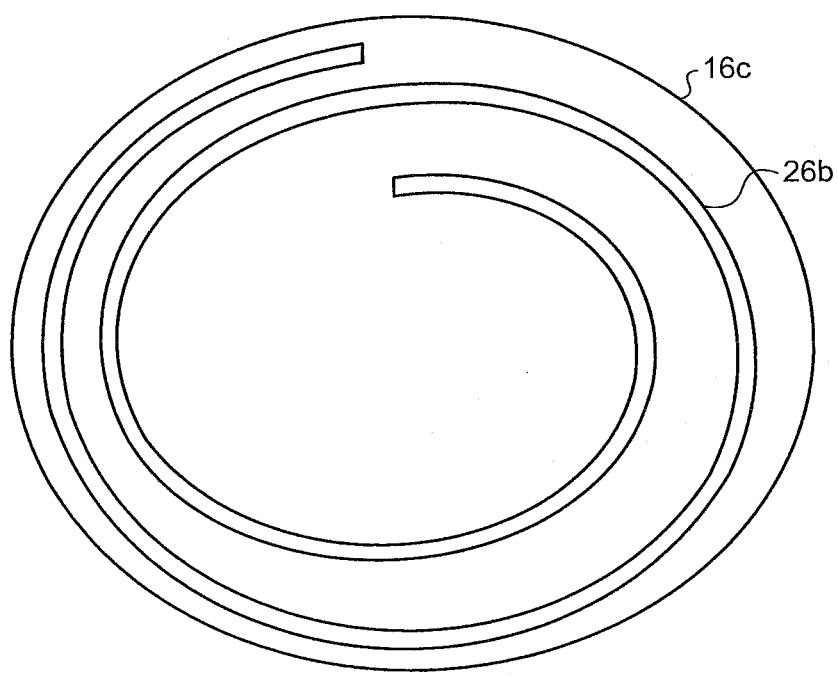
FIG. 5 is a drawing that illustrates a structure of a spiral-shaped antenna conductor.

When the antenna conductor is arranged planarly, thickness h1 of the antenna conductor 16b is preferably smaller than outermost diameter w1 of the antenna conductor as illustrated in FIG. 4. The setting of h1<w1 is preferable because the influence of dielectric loss can be reduced. However, the ratio of h1 to w1 is not limited to that illustrated in FIG. 4. Moreover, the relation h1<w1 can be applied not only to the C-shape but also to other shapes such as the spiral shape.

Figure 8A:
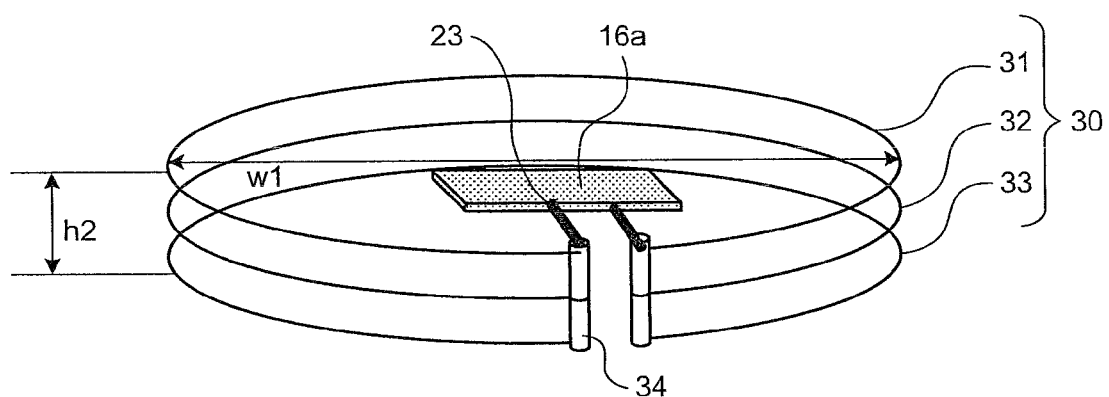
FIGS. 8A and 8B are schematic diagrams of one example of a cubic antenna conductor.
Figure 8B:
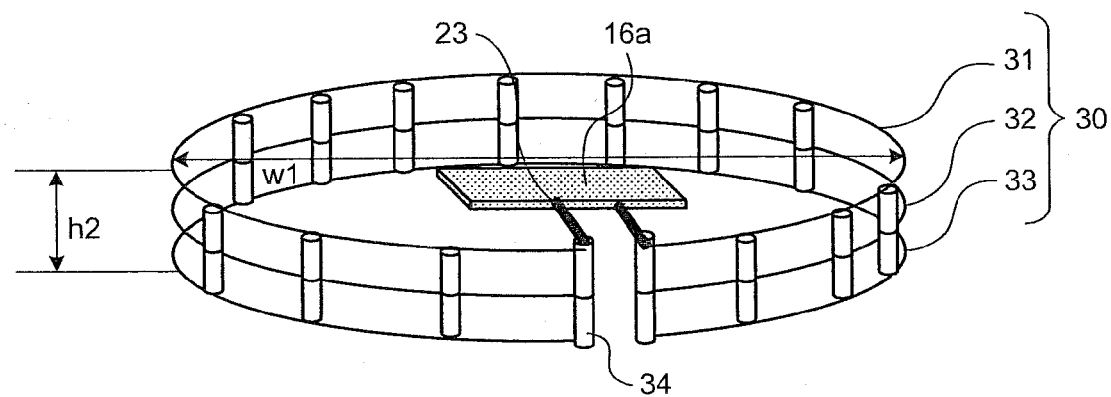

When the antenna conductor is arranged cubically and embedded in the substrate section as illustrated in FIGS. 8A and 8B, height h2 of an antenna conductor 30 is preferably smaller than the outermost diameter w1 of the antenna conductor 30. The setting of h2<w1 is preferable because the influence of dielectric loss can be reduced. However, the ratio of h2 to w1 is not limited to that illustrated in FIGS. 8A and 8B. Moreover, h2<w1 can be applied not only to the C-shape but also to other shapes such as the spiral shape, for example, h2<w1 can be applied to the spiral shape. When the antenna conductor is embedded in the substrate section and arranged cubically, preferably the antenna conductor is 1.5- to 2.5-turn spiral shape, and more preferably a 2-turn spiral shape.

The outermost diameter of the antenna conductor is preferably 60% to 100% of the outermost diameter of the substrate section. Here, 60% or more is preferable because a cross-sectional area of the loop can be made larger, and the decrease of the antenna gain can be restrained.

When the antenna conductor is embedded in the substrate section and arranged cubically, the antenna conductor may be of the shape that continuously draws a spiral. Alternatively, the antenna conductor may include interlayer vias 35, penetration vias or throughholes 34 as illustrated in FIG. 7 to FIG. 10.

Figure 7:
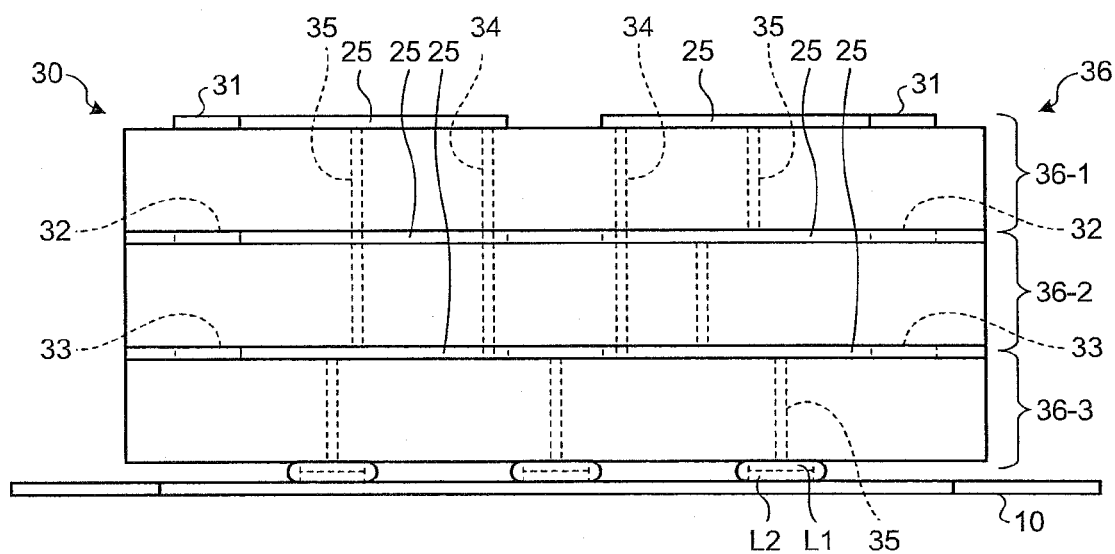
FIG. 7 is a front view of one example of a radio communication unit in which a cubic antenna conductor is formed with a multilayer substrate.

A substrate section 36 illustrated in FIG. 7 includes three layers of substrates (36-1, 36-2, and 36-3). The antenna conductors are formed on the surface of the substrate 36-1, between the substrate 36-1 and the substrate 36-2, and between the substrate 36-2 and the substrate 36-3. A C-shaped antenna conductor 31 formed on the substrate 36-1, a C-shaped antenna conductor 32 formed between the substrate 36-1 and the substrate 36-2, and a C-shaped antenna conductor 33 formed between the substrate 36-2 and the substrate 36-3 are linked together by the interlayer vias 34 to form the cubic antenna conductor 30.

The cubic antenna conductor 30 thus formed is schematically illustrated in FIGS. 8A and 8B. Each of the antenna conductors 31 to 33 is higher in electric conductivity and lower in copper loss compared with the singly-used antenna conductor 31, and as a result, it is possible to improve the radiant efficiency of the antenna. The electric conductivity of the antenna conductor may be further improved by connecting the antenna conductors 31 to 33 by using two or more penetration vias or throughholes 34 as illustrated in FIG. 8B.

Figure 9A:
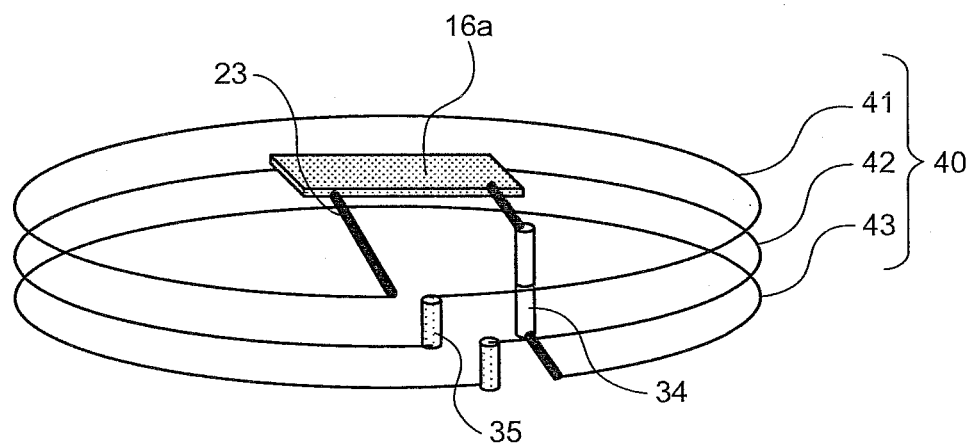
FIGS. 9A and 9B are schematic diagrams of another example of the cubic antenna conductor.
Figure 9B:
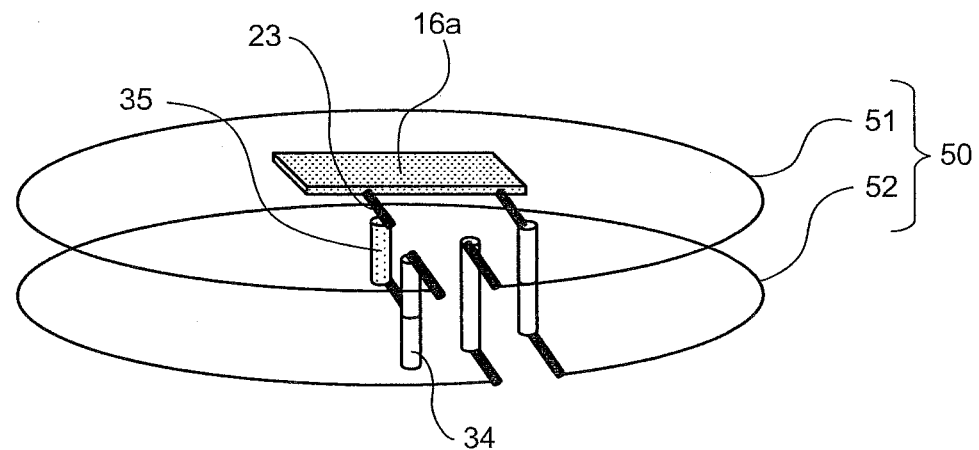

Furthermore, cubic antenna conductors 40 and 50 as illustrated in FIGS. 9A and 9B may be formed by appropriately adjusting layouts and shapes of the antenna conductors, and, layouts of the interlayer vias 35, penetration vias, and throughholes 34. In FIG. 9A, signs 41, 42, and 43 denote the antenna conductor, and the sign 34 denotes the penetration vias or throughholes. The sign 35 denotes the interlayer vias.

In FIG. 9B, signs 51 and 52 denote the antenna conductor; the sign 34 denotes the penetration vias, or throughholes. The sign 35 denotes the interlayer via. In forming a spiral-shaped antenna as illustrated in FIGS. 9A and 9B, an effort is made to devise a shape of the antenna to increase the electric current which flows trough the antenna and thereby to improve the gain of the antenna. Specifically, the effort is made to lower impedance of the antenna by increasing the pitch between the antenna conductors, and reducing the number of turns of the antenna conductor. In a preferable structure, two turns of antenna conductor is formed on a surface where the lands are formed and on a surface where the transmitting circuit 16a is formed, and a pitch between the antenna conductors is set to maximum length, as illustrated in FIG. 9B.

Although the thickness of the antenna conductor is not particularly limited, and can be appropriately decided depending on the purposes, the range from 0.01 to 2 mm is preferable. The thickness of the antenna conductor is preferably 0.01 mm or more because it is possible to reduce the influence of the decrease of conductivity of the antenna conductor, and restrain deterioration of the radiant characteristics of the antenna. The thickness of the antenna conductor is preferably 2 mm or less because the mass of the capsule type medical device can be reduced.

——Transmitting Circuit——

The transmitting circuit is not particularly limited, but the transmitting circuit that corresponds to the purposes can be appropriately used.

The transmitting circuit may include a plurality of elements, and the numbers of the elements and the sizes of the elements are not particularly limited.

The arrangement of the elements is not particularly limited and the elements can be appropriately arranged depending on the purposes, but the elements are preferably arranged 0.5 mm or more apart from the antenna conductor. Thus, the influence against the antenna characteristics can be reduced, because the magnetic field radiated from the antenna is hardly canceled by the magnetic field generated by the eddy current which is induced by the elements and patterns of the transmitting circuit.

As illustrated in FIG. 7, when the substrate section 36 that includes a plurality of substrates (36-1, 36-2, 36-3) is used, each of elements 25 of the transmitting circuit may be electrically linked together by using the interlayer via 35.

In FIG. 1 and FIG. 2, the substrate section 16c is a single-layered rigid circuit board that is formed in a circular disk shape. The C-shaped antenna conductor 16b that functions as a loop antenna is arranged closely attached to one surface of the substrate section 16c, and the transmitting circuit 16a that includes a plurality of circuit elements and circuit patterns is arranged within the internal area E1 surrounded by the antenna conductor 16b. Lands L1 (refer to FIG. 2), which are electrically connected to the transmitting circuit 16a through the interlayer via, the penetration via, or the throughhole, are arranged to the other surface of the substrate section 16c. The lands L1 are provided corresponding to lands L2 which are provided on a flexible substrate 10, and the lands L1 and L2 are joined together by reflow soldering. The antenna of the conventional radio communication unit is made of copper wire which easily deforms by external force to deteriorate the radio characteristics of the antenna. Therefore, conventionally, in the process of connecting the antenna to the substrate and in the process of connecting the radio communication unit to other components, it was impossible to apply the automatic mounting such as reflow soldering, and therefore the mounting had to be done manually. Moreover, the antenna was often deformed during the manual processes of mounting the antenna and the radio communication system, and in the subsequent assembly process. Therefore, it was necessary to conduct the performance test of the antenna after each of the work processes performed after the radio communication unit 16 is mounted. Conversely, in the present invention, the manual mounting process is not required, because the antenna of the radio communication unit 16 is formed in the same manner as a pattern 23 in the manufacturing process of the pattern 23 of the substrate section 16c. Further, as the antenna is arranged closely attached to the substrate section 16c, the antenna is not easily deformed by the external force. As a result, the connection of the radio communication unit 16 with other components can be done with the automatic mounting such as reflow soldering, and therefore the productivity of the antenna and the capsule type medical device can be improved, and the production cost thereof can be reduced. In the present invention, if the tests are conducted before assembly and after the final assembly, there is no need to conduct the performance test of the antenna after each of the work processes performed after the radio communication unit 16 is mounted, and therefore the testability is improved and the test cost can be reduced.

Meanwhile, although the radio communication frequency is not particularly limited and can be appropriately decided depending on the purposes, the UHF band is preferable. As the UHF, the range from 300 MHz to 500 MHz is particularly preferable. For example, if the communication frequency of 450 MHz is used, the wavelength shortening effect occurs, and the wavelength becomes approximately 10 cm, because the relative permittivity of the body tissue is approximately 50, and the relative magnetic permeability of the body tissue is approximately one. The antenna gain improves by approximating the antenna length to the wavelength. Therefore, the antenna length is preferably within a range from approximately half the wavelength to the wavelength.

——Manufacturing Method of Radio Communication Unit——

Although the manufacturing method of the radio communication unit of the present invention is not particularly limited, the radio communication unit can be manufactured by a method illustrated in FIGS. 3A to 3D, for example.

Firstly, the substrate section 16c on which conductive films 21 are formed (FIG. 3A) is prepared.

Figure 3A:
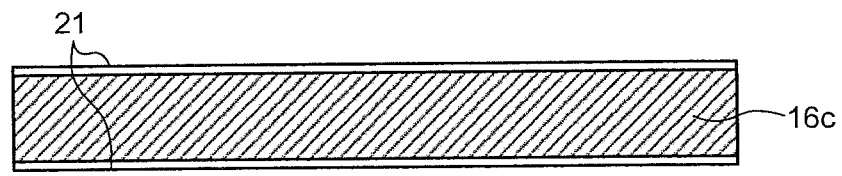
FIGS. 3A to 3D are drawings that illustrate a manufacturing process of the radio communication unit.
Figure 3B:
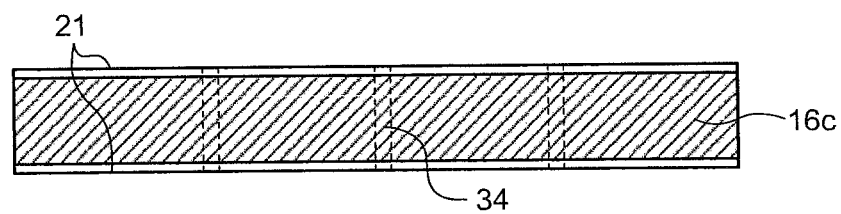

Then, the penetration via or the throughhole 34 are formed, and the penetration via or the throughhole 34 are filled with conducting material that is conductive (FIG. 3B).

Figure 3C:
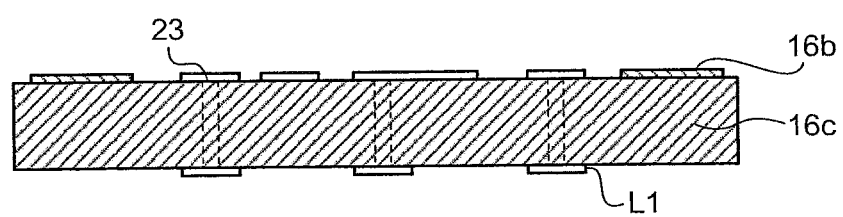

Further, the pattern 23 of the transmitting circuit and the antenna conductor 16b are formed at positions that correspond to the penetration via or the throughhole 34, and the lands L1 are formed at positions that correspond to the penetration via or the throughhole 34 on the surface on which elements 25 of the transmitting circuit are not arranged (FIG. 3C).

Figure 3D:
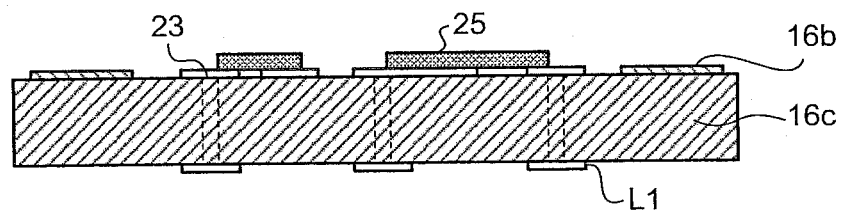

Further, the elements 25 of the transmitting circuit are mounted on the pattern 23 (FIG. 3D).

Although the material of the substrate section 16c used in the aforementioned process of FIG. 3A is not particularly limited, the same material as the aforementioned material of the substrate section can be used, for example. Although the material of the conductive film 21 is not particularly limited, the same material as the aforementioned material of the antenna conductor can be used, for example. Although the forming methods of the pattern 23 of the transmitting circuit and the antenna conductor 16b in the aforementioned process of FIG. 3C are not particularly limited, etching can be used, for example. Furthermore, the pattern 23 of the transmitting circuit and the antenna conductor 16b illustrated in FIG. 3C can be formed by patterning the conductive material on the substrate section 16c of FIG. 3A, using a printing method.

Thus, the elements 25 of the transmitting circuit, the antenna conductor 16b, and the lands L1 are integrally formed with the substrate section 16c. In addition, the volume and shape of the radio communication unit 16 are approximately the same as the volume and shape of the substrate section 16c, thus downsizing of the capsule type medical device is promoted. Further, because the radio communication unit 16 is integrally formed, compared with the conventional cubic antenna conductor, the antenna conductors hardly deforms, whereby the capsule type medical device that can maintain the initial antenna performance is realized.

Figure 10:
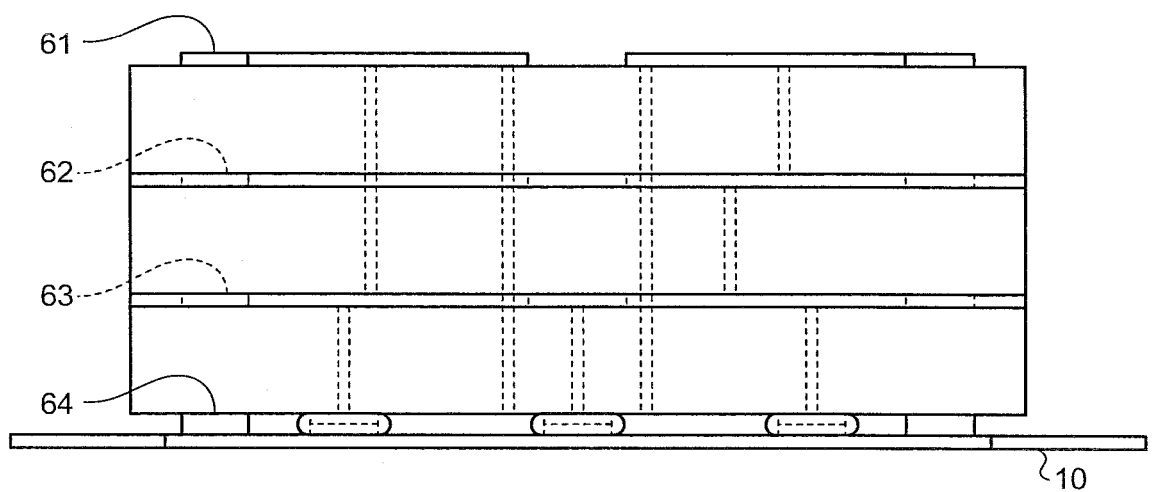
FIG. 10 is a front view of one example of the radio communication unit, in which a cubic antenna conductor is formed by adding the antenna conductors to a flexible substrate.

Meanwhile, as illustrated in FIG. 10, it is possible to simply form a cubic antenna, by forming an antenna conductor 64 on the flexible substrate 10, and connecting the antenna conductor 64 with antenna conductors 61 to 63. The antenna conductors may be formed on the surface on which the lands L1 are provided.

According to the present embodiment, it is possible to accelerate the downsizing and lightening of the radio communication unit 16 without deteriorating the radiant characteristics of the antenna because the transmitting circuit 16a, the antenna conductors 16b, 30, 40, and the lands L1, and the substrate section 16c are integrally formed (here, "integrally formed" should be interpreted as also meaning "embedded").

The capsule type medical device that can apply the radio communication unit of the present invention is explained referring to the drawings in detail below. The present invention is not limited to the description below.

Figure 11:
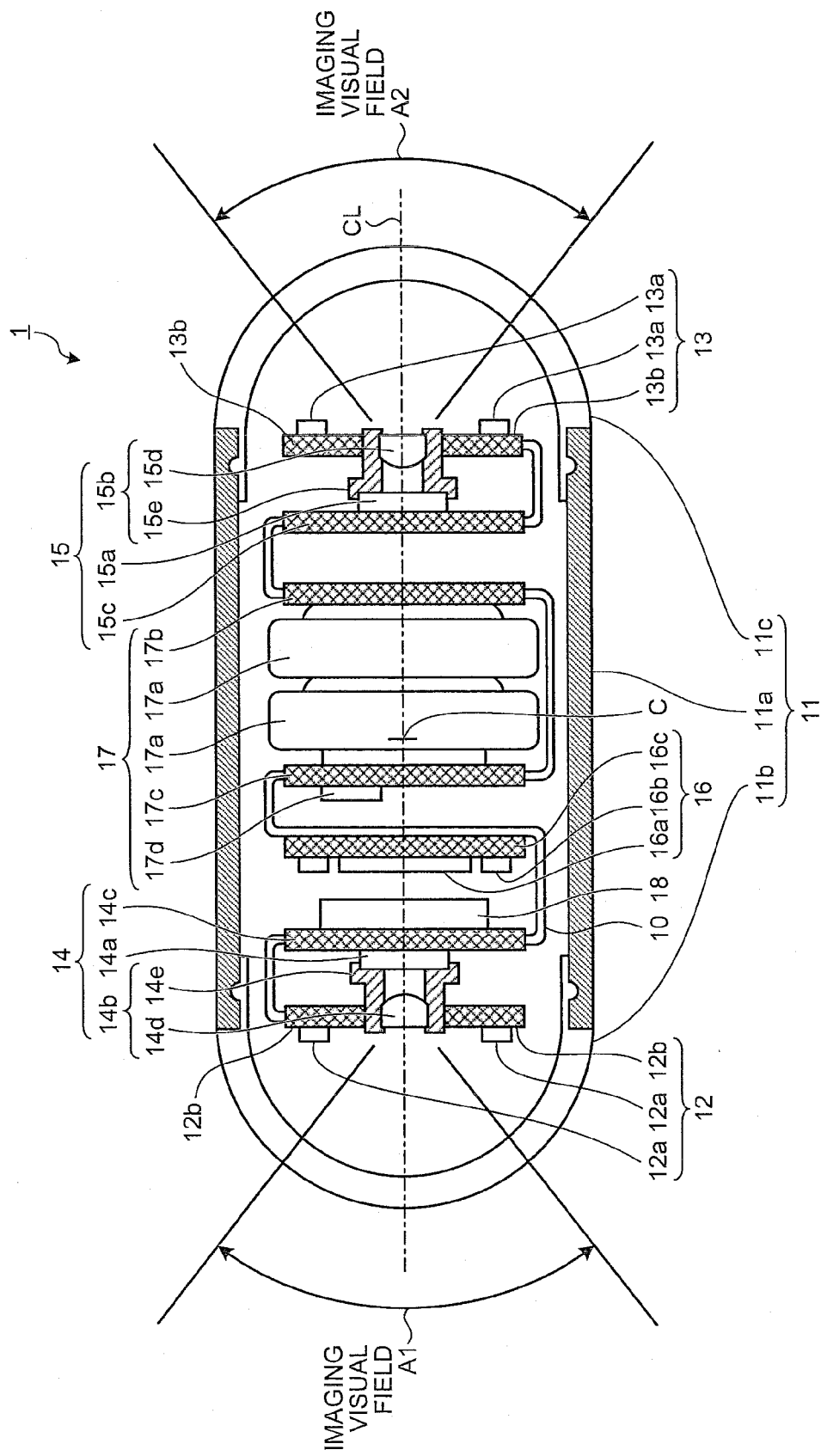
FIG. 11 is a longitudinal cross section that schematically illustrates a capsule type medical device according to an embodiment of the present invention.

FIG. 11 is a schematic longitudinal cross section of a capsule type medical device 1 that applies the radio communication unit 16 of the present invention. The capsule type medical device 1 is introduced into the body of a subject such as patient, acquires the information inside the body of the subject, and transmits the acquired information to the outside by radio.

The capsule type medical device 1 illustrated in FIG. 11 is a multi-lens device, and each lens has directionally different imaging visual field A1 or A2, however the directions of the imaging visual fields and the number of the imaging visual fields are not limited to those illustrated in FIG. 11. The capsule type medical device 1 includes a capsule type casing 11, illuminating units 12 and 13, imaging units 14 and 15, the radio communication unit 16, an electric power source 17, and a control unit 18. The illuminating units 12 and 13 illuminate inside the body of the subject. The imaging units 14 and 15 respectively take images of inside of the body illuminated by the illuminating units 12 and 13. The radio communication unit 16 transmits each of the intra-subject images taken by the imaging units 14 and 15 to the outside by radio communication. The electric power source 17 supplies driving electric power to each of the components of the capsule type medical device 1. The control unit 18 controls each of the components of the capsule type medical device 1. However, the components of the capsule type medical device of the present invention are not limited to the above mentioned components. For example, a structure that does not include the illuminating unit may be possible depending on the function of the imaging unit. The components of the capsule type medical device according to the present invention are described in detail below.

——Casing——

The casing 11 at least plays a role of protecting the internal components of the capsule type medical device 1.

The shape of the casing is not particularly limited. For example, the casing may be a cylindrical component with two domed ends as illustrated in FIG. 11.

The casing 11 may be either integrally formed or shaped in such a way that the casing can be divided into a plurality of sections. The casing 11 illustrated in FIG. 11 includes a cylindrically-structured casing main body 11a and optical domes 11b and 11c.

The casing main body 11a is a cylindrical case having openings at both ends, and houses therein each of the components such as the radio communication unit 16. Although layout of each of the components in the casing 11 is not particularly limited, the illuminating unit 12 and the imaging unit 14 are fixedly arranged in proximity of one open end, whereas the illuminating unit 13 and the imaging unit 15 are fixedly arranged in proximity of the other open end. The radio communication unit 16, the electric power source 17, and the control unit 18 can be arranged in an inner region of the casing main body 11a. The inner region is located between the imaging unit 14 and the imaging unit 15.

The optical domes 11b and 11c are optical members which are formed in dome shape and transmit visual light. Specifically, the optical dome 11b is mounted at one open end of the casing main body 11a, which is the open end on the side of the imaging visual field A1, at which the illuminating unit 12 and the imaging unit 14 are fixedly arranged, and the optical dome 11b closes the open end. The optical dome 11c is mounted at the other open end of the casing main body 11a, which is the open end on the side of the imaging visual field A2, at which the illuminating unit 13 and the imaging unit 15 are fixedly arranged, and the optical dome 11c closes the open end. However, the optical domes do not necessarily transmit the visual light depending on the functions of the imaging unit.

The casing 11, which is formed by the casing main body 11a and the optical domes 11b and 11c on two ends, liquid-tightly houses each of the components (e.g. illuminating units 12 and 13, imaging units 14 and 15, radio communication unit 16, electric power source 17, and control unit 18) of the capsule type medical device 1.

——Illuminating Unit——

The illuminating unit 12 illuminates inside the body of the subject that is imaged by the imaging unit 14. Specifically, the illuminating unit 12 is arranged inside the casing 11 at a side of the optical dome 11b, and illuminates the photographic subject of the imaging unit 14 through the optical dome 11b. The illuminating unit 12 includes a plurality of light-emitting devices 12a that emits illuminating light toward the photographic subject of the imaging unit 14, and an illuminating board 12b on which an electric circuit for realizing the functions of the illuminating unit 12 is formed. However, the illuminating unit is not necessarily included in the capsule type medical device depending on the functions of the imaging unit.

The plurality of light-emitting devices 12a is mounted to the illuminating board 12b and emits the illuminating light toward the imaging visual field A1 of the imaging unit 14 through the optical dome 11b. The plurality of light-emitting devices 12a illuminates the photographic subject (inside the body of the subject within the imaging visual field A1) of the imaging unit 14 with such illuminating light. The illuminating board 12b is, for example, a rigid electric circuit board that is formed in a disk shape, and arranged inside the casing 11 at a side of the optical dome 11b. A lens frame of the imaging unit 14 is inserted into a central part of the illuminating board 12b.

Explanations of the illuminating unit 13, light-emitting devices 13a, illuminating board 13b, and imaging visual field A2 in FIG. 11 are omitted because the explanations are similar to those of the illuminating unit 12, light-emitting devices 12a, illuminating board 12b, and imaging visual field A1.

——Imaging Unit——

The imaging unit 14 has the imaging visual field A1 in an imaging direction that is determined depending on a posture of the casing 11, and takes images of the photographic subject of the imaging visual field A1. Specifically, the imaging unit 14 is fixedly arranged inside the casing 11 at a side of the optical dome 11b, and takes the images of the photographic subject of the imaging visual field A1 (namely, inside the body within the imaging visual field A1) that is illuminated with the illuminating unit 12. The imaging unit 14 includes a solid-state imaging device 14a such as a CCD or a CMOS, an optical system 14b which forms the image of the photographic subject on a light receiving surface of the solid-state imaging device 14a, and an imaging board 14c on which an electric circuit for realizing the functions of the imaging unit 14 is formed.

The solid-state imaging device 14a takes images of the photographic subject that is illuminated with the illuminating unit 12. Specifically, the solid-state imaging device 14a has the imaging visual field A1 in the imaging direction that is determined depending on the posture of the casing 11, and takes images of the photographic subject within the imaging visual field A1 that is illuminated with the illuminating unit 12. More specifically, the solid-state imaging device 14a has the light receiving surface that receives the light that comes from the photographic subject that is present within the imaging visual field A1, and takes the images of a photographic subject (namely, images inside the subject within the imaging visual field A1) by photo-electrically converting the light that comes from the photographic subject and is received by the light receiving surface.

The optical system 14b includes a lens 14d that forms the image of the photographic subject on the light receiving surface of the solid-state imaging device 14a, and a lens frame 14e that holds the lens 14d. The lens 14d collects the light that comes from a photographic subject, which is present within the imaging visual field A1, on the light receiving surface of the solid-state imaging device 14a, and forms the image of the photographic subject on the light receiving surface of the solid-state imaging device 14a.

The lens frame 14e is cylindrically structured and has openings at both ends thereof, and holds the lens 14d inside the cylinder. Specifically, the lens frame 14e holds the lens 14d in the cylinder in proximity of one open end. The other open end of the lens frame 14e is fixed to the solid-state imaging device 14a in such a manner that the light from the photographic subject is lead to the light receiving surface of the solid-state imaging device 14a. The one open end (the side which holds the lens 14d) of the lens frame 14e is inserted into the illuminating board 12b, and fixed to the illuminating board 12b.

The imaging board 14c is a rigid circuit board, formed in a disk shape, for example, and fixedly arranged inside the casing 11 at the side of the optical dome 11b. Specifically, the imaging board 14c is fixedly arranged in proximity of the illuminating board 12b, and closer to the center C of the casing 11 than the illuminating board 12b is. The solid-state imaging device 14a and the control unit 18 are mounted to the imaging board 14c.

However, the imaging unit that is used in the capsule type medical device of the present invention is not limited to the imaging unit that has a function to acquire a visual light image. For example, other than the information that is obtainable from the visual light, the imaging unit having a function of acquiring information from infrared rays, ultraviolet rays, temperature, or sound may be used as a substitute for the aforementioned imaging unit, or may be used together with the aforementioned imaging unit. Explanations of the imaging unit 15, solid-state imaging devices 15a, optical system 15b, imaging board 15c, lens 15d, and lens frame 15e in FIG. 11 are omitted because the explanations are similar to those of the imaging unit 14, solid-state imaging device 14a, optical system 14b, imaging board 14c, lens 14d, and lens frame 14e.

As described above, each of the imaging visual fields A1 and A2 of the imaging units 14 and 15 is determined depending on the posture of the casing 11. For example, the imaging visual fields A1 and A2 respectively cover the photographic subjects (inside the body of the subject) in the opposite directions from the casing 11. In this case, the imaging unit 14 is preferably fixedly arranged in such a manner that an optical axis of the imaging unit 14, which is the central axis of the imaging visual field A1, and a longitudinal central axis CL of the casing 11 are parallel to each other or on the same straight line. The imaging visual field A2 of the imaging unit 15 faces the opposite direction from that of the imaging visual field A1 of the imaging unit 14, and the imaging unit 15 is preferably fixedly arranged in such a manner that an optical axis of the imaging unit 15, which is the central axis of the imaging visual field A2, and the central axis CL are parallel to each other or on the same straight line.

——Radio Communication Unit——

The radio communication unit is as explained earlier.

——Electric Power Source——

The electric power source 17 is, for example, fixedly arranged between the imaging unit 15 and the radio communication unit 16 inside the casing 11, and supplies driving electric power to each of the components of the capsule type medical device 1. The electric power source 17 includes, for example, a battery 17a that has a predetermined electric power, electric power source boards 17b and 17c on which an electric circuit for realizing the function of the electric power source 17 is formed, and a switch 17d that switches between on state and off state of the electric power supply from the battery 17a.

Although the battery 17a is not particularly limited, a button-type battery such as a silver oxide battery may be used, for example. Required number of batteries (for example two) is connected between the electric power source boards 17b and 17c. The electric power source boards 17b and 17c are respectively provided with a positive pole terminal and a negative pole terminal which are electrically connected to the battery 17a. The electric power source boards 17b and 17c and electric circuit boards for each of the components (namely, the illuminating boards 12b and 13b, imaging boards 14c and 15c, and substrate section 16c) of the capsule type medical device 1 are electrically connected by a flexible board or the like. The switch 17d is a reed switch that conducts an on/off switching operation by the external magnetic force, for example, and is mounted to the electric power source board 17c. Specifically, the switch 17d switches between on/off states of the electric power supply from the battery 17a by conducting such on/off switching operations. Thus, the switch 17d controls the electric power supplies to each of the components of the capsule type medical device 1 from the battery 17a.

——Control Unit——

The control unit 18 is mounted to the imaging board 14c, for example, and controls each of the components of the capsule type medical device 1. Specifically, the control unit 18 controls each of the light-emitting devices 12a and 13a of the illuminating units 12 and 13, each of the solid-state imaging devices 14a and 15a of the imaging units 14 and 15, and the transmitting circuit 16a of the radio communication unit 16. More specifically, the control unit 18 controls operation timings of the plurality of light-emitting devices 12a and the solid-state imaging device 14a in such a way that the solid-state imaging device 14a takes images of the photographic subject in the imaging visual field A1 at every predetermined time in synchronization with the light emitting operations of the plurality of the light-emitting devices 12a. Moreover, the control unit 18 controls operation timings of the plurality of light-emitting devices 13a and the solid-state imaging device 15a in such a way that the solid-state imaging device 15a takes images of the photographic subject in the imaging visual field A2 at every predetermined time in synchronization with the light emitting operations of the plurality of the light-emitting devices 13a. The control unit 18 alternately controls the light-emitting device 12a and the solid-state imaging device 14a, and the light-emitting device 13a and the solid-state imaging device 15a at every predetermined time. The control unit 18 has various kinds of parameters such as white balance in relation to the imaging process, and has an image processing function to alternately generate image signals that respectively include images of the photographic subjects that are alternately taken with the solid-state imaging devices 14a and 15a. The control unit 18 alternately transmits image signals that include the intra-subject images to the radio communication unit 16, and controls the transmitting circuit 16a in such a way that the transmitting circuit 16a alternately generates and outputs radio signals that include the intra-subject images. It is possible to add new components or upsize the already existing components in the capsule type casing by using the radio communication unit 16 of the present invention. Moreover, downsizing of the capsule type medical device is possible. In addition, as the antenna has a hardly-deformed shape, handling ability of the antenna improves, and productivity and testability of the antenna and the capsule type medical device can be improved. Thus it is possible to reduce the production cost and inspection cost of the capsule type medical device.

Further, because the antenna conductor of the present invention is lighter than the conventional antenna, the use of the radio communication unit of the present invention can result in a capsule type medical device whose specific gravity is less than one.

In the capsule type medical device of the embodiment, it is possible to secure more space in the capsule type medical device by devising the shape of the antenna which is one of the components of the capsule type medical device.

What is claimed is:

1. A capsule type medical device comprising:
a flexible substrate with a printed circuit; and
a radio communication unit mounted on the flexible substrate,
wherein the radio communication unit comprises:
a substrate section having a rigid substrate with a printed circuit;
an antenna conductor that is arranged on one surface of the rigid substrate;
a transmitting circuit that is arranged on the one surface of the rigid substrate and electrically connected with the antenna conductor by the printed circuit of the rigid substrate; and
a plurality of first lands that are arranged to another surface of the rigid substrate, and electrically connected with the transmitting circuit; and
the flexible substrate includes a plurality of second lands provided on a first surface of the flexible substrate;
wherein the first and second lands are directly joined together.

2. The capsule type medical device according to claim 1, wherein the antenna conductor is C-shaped or spiral-shaped.

3. The capsule type medical device according to claim 1, wherein
the antenna conductor is spiral-shaped,
the number of turns of the antenna conductor is in the range of 1.5 to 2.5 turns, and
at least a part of the antenna conductor is embedded in the substrate section and arranged cubically.

4. The capsule type medical device according to claim 1, wherein when the antenna conductor is arranged planarly, the thickness of the antenna conductor is smaller than the outermost diameter of the antenna conductor.

5. The capsule type medical device according to claim 1, wherein when at least a part of the antenna conductor is embedded in the substrate section and arranged cubically, the height of the antenna conductor is smaller than the outermost diameter of the antenna conductor.

6. The capsule type medical device according to claim 1, wherein the thickness of the antenna conductor is in the range of 0.01 to 2 mm.

7. The capsule type medical device according to claim 1, wherein the substrate section is circular disk-shaped.

8. The capsule type medical device according to claim 1, wherein the outermost diameter of the antenna conductor is in the range of 60% to 100% of the outermost diameter of the substrate section.

9. The capsule type medical device according to claim 1, wherein specific gravity of the capsule type medical device is less than one.

10. The capsule type medical device according to claim 1, wherein the transmitting circuit is surrounded by the antenna conductor.

11. The capsule type medical device according to claim 1, wherein the substrate section includes first and second substrates;
the capsule type medical device further comprises:
a first antenna conductor arranged on a surface of the first substrate; and
a second antenna conductor arranged between the first and second substrates, wherein
the first and second antenna conductors are linked together to form a cubic antenna conductor.

* * * * *